United States Patent
Yeh et al.

(10) Patent No.: US 7,718,849 B2
(45) Date of Patent: May 18, 2010

(54) USE OF A TOSPOVIRAL NUCLEID ACID MOLECULE FOR BROAD-SPECTRUM TRANSGENIC RESISTANCE AGAINST DIFFERENT TOSPOVIRUSES

(76) Inventors: Shyi-Dong Yeh, No. 250, Guoguang Rd., S. District, Taichung (TW); Tsung-Chi Chen, No. 250, Guoguang Rd., S. District, Taichung (TW)

( * ) Notice: Subject to any disclaimer, the term of this patent is extended or adjusted under 35 U.S.C. 154(b) by 59 days.

(21) Appl. No.: 11/878,912

(22) Filed: Jul. 27, 2007

(65) Prior Publication Data

US 2009/0031447 A1      Jan. 29, 2009

(51) Int. Cl.
*C12N 15/82*    (2006.01)
*A01H 1/00*    (2006.01)
*C12N 15/87*    (2006.01)

(52) U.S. Cl. .................................................... 800/280

(58) Field of Classification Search ........................ None
See application file for complete search history.

(56) References Cited

OTHER PUBLICATIONS

Bucher et al. 2006 Journal of general Virology 87:3697-3701.*
Yeh et al. 2005 Broad-spectrum resistance to distinct tospoviruses in transgenic tobacco carrying the conserved region of the L protein of Watermelon silver mottle virus. VIII International Symposium on Thysanoptera and Tospoviruses, Abstracts of Plenary Session III, Thrips and Tospovirus Management, p. 62.*
Yeh, et al., "VIII International Symposium on Thysanoptera and Tospoviruses", Journal of Insect Science, 7:28, 1536-2442.

* cited by examiner

*Primary Examiner*—Anne Kubelik
*Assistant Examiner*—Li Zheng
(74) *Attorney, Agent, or Firm*—Fei-Fei Chao; Andrews Kurth

(57) ABSTRACT

A method of using a tospoviral nucleic acid molecule of the sequence of nt (nucleotide) 3975-4928 in accordance with GenBank Accession No. AF133128 or a full complement thereof comprising the steps of: (a) obtaining at least one fragment made from the tospoviral nucleic acid molecule; (b) obtaining a transgene from the at least one fragment; (c) introducing the transgene into a plant to generate a transgenic plant; (d) culturing the transgenic plant; (e) selecting a transgenic plant with broad-spectrum resistance; and (f) obtaining the transgenic plant with broad-spectrum resistance.

1 Claim, 1 Drawing Sheet

FIG.1

SEQUENCE LISTING

<160> NUMBER OF SEQ ID NOS: 18

<210> SEQ ID NO 1
<211> LENGTH: 30
<212> TYPE: DNA

-continued

```
<213> ORGANISM: Artificial
<220> FEATURE:
<223> OTHER INFORMATION: Synthesized
<400> SEQUENCE: 1
gccatggagc acacatacaa gcatatcgcc 30

<210> SEQ ID NO 2
<211> LENGTH: 30
<212> TYPE: DNA
<213> ORGANISM: Artificial
<220> FEATURE:
<223> OTHER INFORMATION: Synthesized
<400> SEQUENCE: 2
gagctcgagt cgttctcttc tcctggcagc 30

<210> SEQ ID NO 3
<211> LENGTH: 954
<212> TYPE: DNA
<213> ORGANISM: Watermelon spotted wilt virus
<400> SEQUENCE: 3
gagcacacat acaagcatat cgcccaatct gatccttctg aggcaatatc tatatctgga 60
gattacaaaa taaagaactt agcatcactg tcatatgata ctataactaa ctataacaca 120
gcacttcaaa agaacctgga atgtaaaatg gctttcttgt cggcagatca atcaaagtgg 180
tctgcatcag atttaaccta caaatacata ctagctgtta taatgaaccc tatattgacc 240
actggagaga taaacttgat gtgtgaatgc ataatgatgt atataaagtt aaagagggtg 300
tgcatcccta ctgatatatt cctaaacctt aaaagaggtc aaacagagta cgggtcttat 360
gggactgctt tatctgtatt gacagataat ttggaaacaa acacattccc agtgtctatg 420
aactggctac aagggaatct caattattta tcatctgtct accattcttg tgccatgata 480
ggttatgaaa aagcaatgaa aaagatgaaa gattatgatt ttacaataag atggatggta 540
cactctgatg ataatgctac atctatagta gtcagaggag acttaaagaa actttttgtcc 600
agctttaact gttctagtct gtctgaattg ctgttccgga gtattcagtc acattttaaa 660
agttactgta taacactgaa ccctaagaaa agttatgcat cagaatctga agttgaattc 720
atatcagaaa gaattattaa tggtgctgtg atacctctgt actgtaggca tttggccaac 780
tgcagcacag aaagctctca taatagttat tttgacgatt tgatgtctct ttctattcat 840
attacaatgc ttttaagaaa gggttgcccc aatgaattga taccatttgc ttatgcagca 900
atacaagttc agtcacttag catatattca atgctgccag gagaagagaa cgac 954

<210> SEQ ID NO 4
<211> LENGTH: 968
<212> TYPE: DNA
<213> ORGANISM: Artificial
<220> FEATURE:
<223> OTHER INFORMATION: Synthesized
<400> SEQUENCE: 4
gccatggagc acacatacaa gcatatcgcc caatctgatc cttctgaggc aatatctata 60
tctggagatt acaaaataaa gaacttagca tcactgtcat atgatactat aactaactat 120
aacacagcac ttcaaaagaa cctggaatgt aaaatggctt tcttgtcggc agatcaatca 180
aagtggtctg catcagattt aacctacaaa tacatactag ctgttataat gaaccctata 240
ttgaccactg gagagataaa cttgatgtgt gaatgcataa tgatgtatat aaagttaaag 300
```

```
agggtgtgca tccctactga tatattccta aaccttaaaa gaggtcaaac agagtacggg    360
tcttatggga ctgctttatc tgtattgaca gataatttgg aaacaaacac attcccagtg    420
tctatgaact ggctacaagg gaatctcaat tatttatcat ctgtctacca ttcttgtgcc    480
atgataggtt atgaaaaagc aatgaaaaag atgaaagatt atgattttac aataagatgg    540
atggtacact ctgatgataa tgctacatct atagtagtca gaggagactt aaagaaactt    600
ttgtccagct ttaactgttc tagtctgtct gaattgctgt tccggagtat tcagtcacat    660
tttaaaagtt actgtataac actgaacccct aagaaaagtt atgcatcaga atctgaagtt    720
```

-continued

```
Phe Ile Ser Glu Arg Ile Ile Asn Gly Ala Val Ile Pro Leu Tyr Cys
                245                 250                 255

Arg His Leu Ala Asn Cys Ser Thr Glu Ser Ser His Asn Ser Tyr Phe
            260                 265                 270

Asp Asp Leu Met Ser Leu Ser Ile His Ile Thr Met Leu Leu Arg Lys
        275                 280                 285

Gly Cys Pro Asn Glu Leu Ile Pro Phe Ala Tyr Ala Ala Ile Gln Val
    290                 295                 300

Gln Ser Leu Ser Ile Tyr Ser Met Leu Pro Gly Glu Glu Asn Asp Ser
305                 310                 315                 320

Ser

<210> SEQ ID NO 6
<211> LENGTH: 39
<212> TYPE: DNA
<213> ORGANISM: Artificial
<220> FEATURE:
<223> OTHER INFORMATION: Synthesize

<400> SEQUENCE: 6
gccatggaat aataggagca cacatacaag catatcgcc                              39

<210> SEQ ID NO 7
<211> LENGTH: 38
<212> TYPE: DNA
<213> ORGANISM: Artificial
<220> FEATURE:
<223> OTHER INFORMATION: Synthesized

<400> SEQUENCE: 7
gccatggata ataggagcac acatacaagc atatcgcc                               38

<210> SEQ ID NO 8
<211> LENGTH: 977
<212> TYPE: DNA
<213> ORGANISM: Artificial
<220> FEATURE:
<223> OTHER INFORMATION: Synthesized

<400> SEQUENCE: 8
gccatggaat aataggagca cacatacaag catatcgccc aatctgatcc ttctgaggca        60
atatctatat ctggagatta caaaataaag aacttagcat cactgtcata tgatactata       120
actaactata acacagcact tcaaaagaac ctggaatgta aatggctttt cttgtcggca       180
gatcaatcaa agtggtctgc atcagattta acctacaaat acatactagc tgttataatg       240
aaccctatat tgaccactgg agagataaac ttgatgtgtg aatgcataat gatgtatata       300
aagttaaaga gggtgtgcat ccctactgat atattcctaa accttaaaag aggtcaaaca       360
gagtacgggt cttatgggac tgctttatct gtattgacag ataatttgga aacaaacaca       420
ttcccagtgt ctatgaactg gctacaaggg aatctcaatt atttatcatc tgtctaccat       480
tcttgtgcca tgataggtta tgaaaaagca atgaaaaaga tgaaagatta tgattttaca       540
ataagatgga tggtacactc tgatgataat gctacatcta gtagtcag aggagactta         600 aagaaacttt tgtccagctt taactgttct agtctgtctg aattgctgtt ccggagtatt       660
cagtcacatt ttaaaagtta ctgtataaca ctgaacccta agaaaagtta tgcatcagaa       720
tctgaagttg aattcatatc agaaagaatt attaatggtg ctgtgatacc tctgtactgt       780
aggcatttgg ccaactgcag cacagaaagc tctcataata gttatttga cgatttgatg       840
```

```
tctctttcta ttcatattac aatgctttta agaaagggtt gccccaatga attgatacca      900
tttgcttatg cagcaataca agttcagtca cttagcatat attcaatgct gccaggagaa      960
gagaacgact cgagctc                                                    977

<210> SEQ ID NO 9
<211> LENGTH: 976
<212> TYPE: DNA
<213> ORGANISM: Artificial
<220> FEATURE:
<223> OTHER INFORMATION: Synthesize

<400> SEQUENCE: 9
gccatggata taggagcac acatacaagc atatcgccca atctgatcct tctgaggcaa        60
tatctatatc tggagattac aaaataaaga acttagcatc actgtcatat gatactataa      120
ctaactataa cacagcactt caaaagaacc tggaatgtaa aatggctttc ttgtcggcag      180
atcaatcaaa gtggtctgca tcagatttaa cctacaaata catactagct gttataatga      240
accctatatt gaccactgga gagataaact tgatgtgtga atgcataatg atgtatataa      300
agttaaagag ggtgtgcatc cctactgata tattcctaaa ccttaaaaga ggtcaaacag      360
agtacgggtc ttatgggact gctttatctg tattgacaga taatttggaa acaaacacat      420
tcccagtgtc tatgaactgg ctacaaggga atctcaatta tttatcatct gtctaccatt      480
cttgtgccat gataggttat gaaaaagcaa tgaaaaagat gaaagattat gatttttacaa    540 taagatggat ggtacactct gatgataatg ctacatctat agtagtcaga ggagacttaa      600
agaaactttt gtccagcttt aactgttcta gtctgtctga attgctgttc cggagtattc      660
agtcacattt taaagttac tgtataacac tgaaccctaa gaaaagttat gcatcagaat       720
ctgaagttga attcatatca gaaagaatta ttaatggtgc tgtgatacct ctgtactgta      780
ggcatttggc caactgcagc acagaaagct ctcataatag ttatttttgac gatttgatgt    840 ctctttctat tcatattaca atgctttttaa gaaagggttg ccccaatgaa ttgataccat     900
ttgcttatgc agcaatacaa gttcagtcac ttagcatata ttcaatgctg ccaggagaag      960
agaacgactc gagctc                                                    976

<210> SEQ ID NO 10
<211> LENGTH: 28
<212> TYPE: DNA
<213> ORGANISM: Artificial
<220> FEATURE:
<223> OTHER INFORMATION: Synthesize

<400> SEQUENCE: 10
ccatgggtcg ttctcttctc ctggcagc                                         28

<210> SEQ ID NO 11
<211> LENGTH: 30
<212> TYPE: DNA
<213> ORGANISM: Artificial
<220> FEATURE:
<223> OTHER INFORMATION: Synthesize

<400> SEQUENCE: 11
gagctcgagc acacatacaa gcatatcgcc                                       30

<210> SEQ ID NO 12
<211> LENGTH: 966
<212> TYPE: DNA
```

<213> ORGANISM: Artificial
<220> FEATURE:
<223> OTHER INFORMATION: Synthesize

<400> SEQUENCE: 12

| | | | | | |
|---|---|---|---|---|---|
| ccatgggtcg | ttctcttctc | ctggcagcat | tgaatatatg | ctaagtgact | gaacttgtat | 60 |
| tgctgcataa | gcaaatggta | tcaattcatt | ggggcaaccc | tttcttaaaa | gcattgtaat | 120 |
| atgaatagaa | agagacatca | aatcgtcaaa | ataactatta | tgagagcttt | ctgtgctgca | 180 |
| gttggccaaa | tgcctacagt | acagaggtat | cacagcacca | ttaataattc | tttctgatat | 240 |
| gaattcaact | tcagattctg | atgcataact | tttcttaggg | ttcagtgtta | tacagtaact | 300 |
| tttaaaatgt | gactgaatac | tccggaacag | caattcagac | agactagaac | agttaaagct | 360 |
| ggacaaaagt | ttctttaagt | ctcctctgac | tactatagat | gtagcattat | catcagagtg | 420 |
| taccatccat | cttattgtaa | aatcataatc | tttcatcttt | ttcattgctt | tttcataacc | 480 |
| tatcatggca | caagaatggt | agacagatga | taaataattg | agattccctt | gtagccagtt | 540 |
| catagacact | gggaatgtgt | ttgtttccaa | attatctgtc | aatacagata | aagcagtccc | 600 |
| ataagacccg | tactctgttt | gacctctttt | aaggtttagg | aatatatcag | tagggatgca | 660 |
| caccctcttt | aactttatat | acatcattat | gcattcacac | atcaagttta | tctctccagt | 720 |
| ggtcaatata | gggttcatta | taacagctag | tatgtatttg | taggttaaat | ctgatgcaga | 780 |
| ccactttgat | tgatctgccg | acaagaaagc | cattttacat | tccaggttct | tttgaagtgc | 840 |
| tgtgttatag | ttagttatag | tatcatatga | cagtgatgct | aagttcttta | ttttgtaatc | 900 |
| tccagatata | gatattgcct | cagaaggatc | agattgggcg | atatgcttgt | atgtgtgctc | 960 |
| gagctc | | | | | 966 |

<210> SEQ ID NO 13
<211> LENGTH: 32
<212> TYPE: DNA
<213> ORGANISM: Artificial
<220> FEATURE:
<223> OTHER INFORMATION: Synthesize

<400> SEQUENCE: 13

| | | |
|---|---|---|
| atgctctaga gtcgttctct tctcctggca gc | | 32 |

<210> SEQ ID NO 14
<211> LENGTH: 35
<212> TYPE: DNA
<213> ORGANISM: Artificial
<220> FEATURE:
<223> OTHER INFORMATION: Synthesize

<400> SEQUENCE: 14

| | | |
|---|---|---|
| ccggccatgg agagcaatga gcacacatac aagca | | 35 |

<210> SEQ ID NO 15
<211> LENGTH: 982
<212> TYPE: DNA
<213> ORGANISM: Artificial
<220> FEATURE:
<223> OTHER INFORMATION: Synthesize

<400> SEQUENCE: 15

| | | | | | |
|---|---|---|---|---|---|
| atgctctaga | gtcgttctct | tctcctggca | gcattgaata | tatgctaagt | gactgaactt | 60 |
| gtattgctgc | ataagcaaat | ggtatcaatt | cattggggca | accctttctt | aaaagcattg | 120 |
| taatatgaat | agaaagagac | atcaaatcgt | caaaataact | attatgagag | ctttctgtgc | 180 |

```
tgcagttggc caaatgccta cagtacagag gtatcacagc accattaata attctttctg      240
atatgaattc aacttcagat tctgatgcat aacttttctt agggttcagt gttatacagt      300
aacttttaaa atgtgactga atactccgga acagcaattc agacagacta gaacagttaa      360
agctggacaa aagtttcttt aagtctcctc tgactactat agatgtagca ttatcatcag      420
agtgtaccat ccatcttatt gtaaaatcat aatctttcat cttttcatt gcttttcat       480 aacctatcat ggcacaagaa tggtagacag atgataaata attgagattc ccttgtagcc      540
agttcataga cactgggaat gtgtttgttt ccaaattatc tgtcaataca gataaagcag      600
tcccataaga cccgtactct gtttgacctc ttttaaggtt taggaatata tcagtaggga     660
tgcacaccct ctttaacttt atatacatca ttatgcattc acacatcaag tttatctctc      720
cagtggtcaa tatagggttc attataacag ctagtatgta tttgtaggtt aaatctgatg      780
cagaccactt tgattgatct gccgacaaga aagccatttt acattccagg ttcttttgaa      840
gtgctgtgtt atagttagtt atagtatcat atgacagtga tgctaagttc tttatttgt       900 aatctccaga tatagatatt gcctcagaag gatcagattg ggcgatatgc ttgtatgtgt      960
gctcattgct ctccatggcc gg                                               982

<210> SEQ ID NO 16
<211> LENGTH: 1939
<212> TYPE: DNA
<213> ORGANISM: Artificial
<220> FEATURE:
<223> OTHER INFORMATION: Synthesize

<400> SEQUENCE: 16
atgctctaga gtcgttctct tctcctggca gcattgaata tatgctaagt gactgaactt       60
gtattgctgc ataagcaaat ggtatcaatt cattggggca acccttcttt aaaagcattg      120
taatatgaat agaagagac atcaaatcgt caaataact attatgagag ctttctgtgc       180
tgcagttggc caaatgccta cagtacagag gtatcacagc accattaata attctttctg      240
atatgaattc aacttcagat tctgatgcat aacttttctt agggttcagt gttatacagt      300
aacttttaaa atgtgactga atactccgga acagcaattc agacagacta gaacagttaa      360
agctggacaa aagtttcttt aagtctcctc tgactactat agatgtagca ttatcatcag      420
agtgtaccat ccatcttatt gtaaaatcat aatctttcat cttttcatt gcttttcat       480 aacctatcat ggcacaagaa tggtagacag atgataaata attgagattc ccttgtagcc      540
agttcataga cactgggaat gtgtttgttt ccaaattatc tgtcaataca gataaagcag      600
tcccataaga cccgtactct gtttgacctc ttttaaggtt taggaatata tcagtaggga     660
tgcacaccct ctttaacttt atatacatca ttatgcattc acacatcaag tttatctctc      720
cagtggtcaa tatagggttc attataacag ctagtatgta tttgtaggtt aaatctgatg      780
cagaccactt tgattgatct gccgacaaga aagccatttt acattccagg ttcttttgaa      840
gtgctgtgtt atagttagtt atagtatcat atgacagtga tgctaagttc tttatttgt       900 aatctccaga tatagatatt gcctcagaag gatcagattg ggcgatatgc ttgtatgtgt      960
gctcattgct ctccatggag cacacataca agcatatcgc ccaatctgat ccttctgagg     1020
caatatctat atctggagat tacaaaataa agaacttagc atcactgtca tatgatacta     1080
taactaacta taacacagca cttcaaaaga acctggaatg taaaatggct ttcttgtcgg     1140
cagatcaatc aaagtggtct gcatcagatt taacctacaa atacatacta gctgttataa     1200
```

```
tgaaccctat attgaccact ggagagataa acttgatgtg tgaatgcata atgatgtata    1260
taaagttaaa gagggtgtgc atccctactg atatattcct aaaccttaaa agaggtcaaa    1320
cagagtacgg gtcttatggg actgctttat ctgtattgac agataatttg gaaacaaaca    1380
cattcccagt gtctatgaac tggctacaag ggaatctcaa ttatttatca tctgtctacc    1440
attcttgtgc catgataggt tatgaaaaag caatgaaaaa gatgaaagat tatgatttta    1500
caataagatg gatggtacac tctgatgata atgctacatc tatagtagtc agaggagact    1560
taaagaaact tttgtccagc tttaactgtt ctagtctgtc tgaattgctg ttccggagta    1620
ttcagtcaca ttttaaaagt tactgtataa cactgaaccc taagaaaagt tatgcatcag    1680
aatctgaagt tgaattcata tcagaaagaa ttattaatgg tgctgtgata cctctgtact    1740
gtaggcattt ggccaactgc agcacagaaa gctctcataa tagttatttt gacgatttga    1800
tgtctctttc tattcatatt acaatgcttt taagaaaggg ttgccccaat gaattgatac    1860
catttgctta tgcagcaata caagttcagt cacttagcat atattcaatg ctgccaggag    1920
aagagaacga ctcgagctc                                                1939

<210> SEQ ID NO 17
<211> LENGTH: 24
<212> TYPE: DNA
<213> ORGANISM: Artificial
<220> FEATURE:
<223> OTHER INFORMATION: Synthesize

<400> SEQUENCE: 17
atgattgaac aagatggatt gcac                                          24

<210> SEQ ID NO 18
<211> LENGTH: 24
<212> TYPE: DNA
<213> ORGANISM: Artificial
<220> FEATURE:
<223> OTHER INFORMATION: Synthesize

<400> SEQUENCE: 18
gaagaactcg tcaagaaggc gata                                          24
```

USE OF A TOSPOVIRAL NUCLEID ACID MOLECULE FOR BROAD-SPECTRUM TRANSGENIC RESISTANCE AGAINST DIFFERENT TOSPOVIRUSES

BACKGROUND OF THE INVENTION

1. Field of the Invention

The present invention relates to a use of a tospoviral nucleic acid molecule, particularly to a use of a tospoviral nucleic acid molecule for providing broad-spectrum resistance in transgenic plants against different virus species of the genus *Tospovirus*.

2. Description of the Prior Art

Members of the genus *Tospovirus* are transmitted by thrips in a persistent manner to infect more than 900 species in 82 families of monocots and dicots, and they cause severe damages to many important economic crops around the world. Since thrips species are more abundant in tropical and subtropical areas, more tospovirus species are found in these regions. Due to the high divergence of tospoviruses and the persistent transmission by thrips, so far no significant control strategies are available. Tospoviruses have become economically important plant disease agents in the cultivation of crops all over the world.

A tospovirus has an N (nucleocapsid) gene and an NSm gene. The N gene encodes a tospoviral N (nucleocapsid) protein. The NSm gene encodes a tospoviral nonstructural NSm protein.

A conventional method for generating resistance in tospoviral host plants against tospoviruses has been developed. The conventional method comprises following steps:

(a) Preparing a transgene. The transgene comprises the N gene.

(b) Preparing a transgenic plant by introducing the transgene into a tospoviral host plant.

(c) Allowing the N protein to be expressed in the transgenic plant to produce resistance against tospoviruses.

In an embodiment of the conventional method, the tospoviral host plant used in the conventional method is a tobacco plant. The transgenic plant is a transgenic tobacco plant prepared by introducing a transgene having a tospoviral N gene into a tobacco plant, wherein the N gene is derived from a TSWV isolate. High levels of expressed N protein are accumulated in the transgenic tobacco plants. When challenged with different tospoviral inocula, the transgenic tobacco plants show a broad-spectrum resistance not only against the homologous TSWV isolate but also against heterologous INSV isolates. However, the resistance only provides low levels of protection and can be overcome by increasing inoculum strength.

On the other hand, another conventional method uses a transgenic plant carrying a nontranslatable N gene or NSm gene from a tospovirus. This conventional method triggers RNA-mediated resistance to tospoviruses. The specificity of RNA-mediated resistance appears to be highly protective but functional only against the homologous tospovirus from which the N gene or the NSm gene is originated.

To overcome the shortcomings of the conventional methods, the present invention provides a use of a tospoviral nucleic acid molecule in transgenic plants for conferring high levels of broad-spectrum resistance, including immunity, against different tospovirus species to mitigate or obviate the aforementioned problems.

SUMMARY OF THE INVENTION

The main objective of the invention is to provide a use of a tospoviral nucleic acid molecule in a transgenic plant for providing high levels of broad-spectrum resistance against homologous and heterologous tospoviruses in plants.

The use of a tospoviral nucleic acid molecule in accordance with the present invention uses a tospoviral nucleic acid molecule of the sequence of nt (nucleotide) 3975-4928 in accordance with GenBank Accession No. AF133128 or a full complement thereof comprising the steps of:

(a) obtaining at least one fragment made from the tospoviral nucleic acid molecule;

(b) obtaining a transgene from the at least one fragment;

(c) introducing the transgene into a plant to generate a transgenic plant;

(d) culturing the transgenic plant;

(e) selecting a transgenic plant with broad-spectrum resistance; and (f) obtaining the transgenic plant with broad-spectrum resistance.

Other objectives, advantages and novel features of the invention will become more apparent from the following detailed description when taken in conjunction with the accompanying drawings.

BRIEF DESCRIPTION OF THE DRAWINGS

Figure 1:
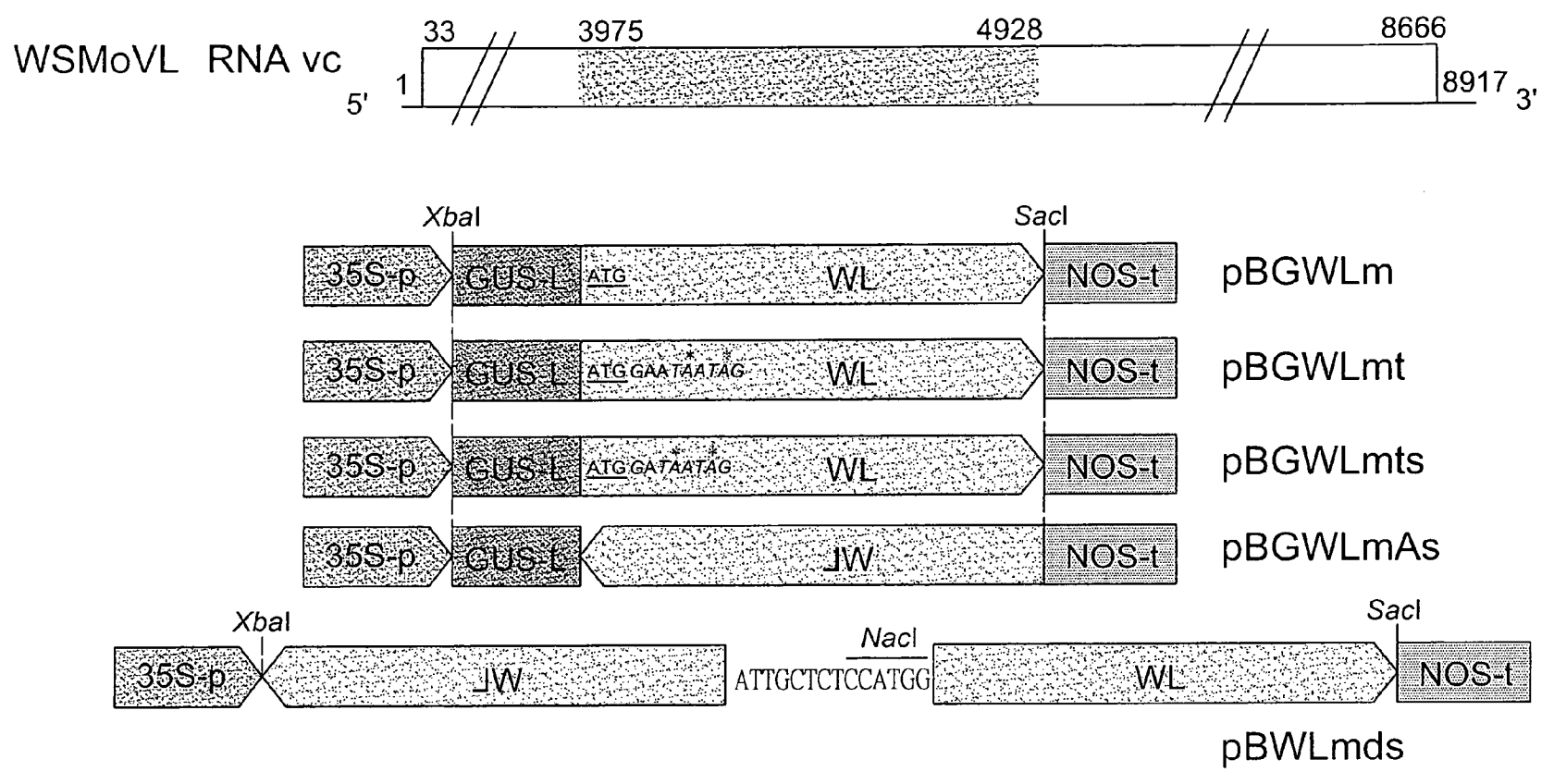

FIG. 1 is a schematic diagram of transgenes.

DETAILED DESCRIPTION OF THE PREFERRED EMBODIMENTS

Members of the genus *Tospovirus* are the only plant-infecting viruses in the family Bunyaviridae. The viruses classified into the genus *Tospovirus* have quasi-spherical, lipoprotein-enveloped particles with diameters ranging from 80 to 110 nm and a tripartite ssRNA (single-stranded ribonucleic acid) genome with three RNAs. The three RNAs are respectively designated as L RNA, M RNA and S RNA. When having infected inside a host cell, each of the RNAs may be formed as a v (viral) strand or as a vc (viral-complementary) strand, wherein the vc strand is complementary to the v strand. When the RNAs are replicated, a v strand is replicated into a vc strand and vice versa. The L RNA is of negative polarity and encodes a large putative RNA-dependent RNA polymerase (RdRp) in the vc strand for virus replication. The M RNA contains two open reading frames (ORFs) in ambisense organization. The S RNA also contains two open reading frames (ORFs) in ambisense organization. The v strand of the M RNA encodes the nonstructural NSm protein for cell-to-cell movement of non-enveloped ribonucleocapsid structures. The vc strand of the M RNA encodes the precursor of $G_N$ and $G_C$ glycoproteins for composing spikes on the viral envelope. The v strand of S RNA encodes a nonstructural NSs protein that forms filamentous inclusion bodies and is a gene-silencing suppressor responsible for the pathogenicity of tospoviruses. The vc strand of the S RNA encodes the N (nucleocapsid) protein that encapsidates tospoviral RNAs. Serological relationships and phylogenetic analysis of N proteins indicate that the current tospovirus species are classified into three major serogroups, such as Tomato spotted wilt virus (TSWV), Watermelon silver mottle virus (WSMoV) and Iris yellow spot virus (IYSV) serogroups, and four distinct serotypes, including Impatiens necrotic spot virus (INSV), Peanut yellow spot virus (PYSV), Peanut chlorotic fan-spot virus (PCFV) and Melon yellow spot virus (MYSV).

So far, there are sixteen recognized tospoviral species in the genus *Tospovirus*. The complete genomes of only four of the sixteen tospoviruses in the genus *Tospovirus*, TSWV, INSV, WSMoV and PBNV, had been determined. Comparison of genomes of these four tospoviruses revealed an RdRp conserved region containing five replicase motifs. Based on the RdRp conserved region, genus-specific degenerate primers were designed for detecting tospoviruses. Recently, the genomes of other two more tospoviruses, CaCV and MYSV, have also been completely determined. With reference to Table 1, the genomes of CaCV and MYSV were also aligned with the genomes of TSWV, INSV, WSMoV and PBNV to confirm the RdRp conserved region of tospoviruses.

TABLE 1

| Virus | Conserved region | | Motif A | | Motif B | |
|---|---|---|---|---|---|---|
| | nt (%) | aa (%) | nt (%) | aa (%) | nt (%) | aa (%) |
| CaCV | 82.9 | 95.9 | 88.2 | 100 | 84.1 | 100 |
| PBNV | 82.6 | 96.9 | 88.2 | 100 | 87.0 | 100 |
| MYSV | 79.4 | 93.7 | 80.4 | 100 | 89.9 | 100 |
| TSWV | 69.0 | 66.7 | 80.0 | 76.5 | 78.3 | 100 |
| INSV | 66.4 | 72.6 | 75.5 | 82.4 | 81.2 | 100 |

| Virus | Motif C | | Motif D | | Motif E | |
|---|---|---|---|---|---|---|
| | nt (%) | aa (%) | nt (%) | aa (%) | nt (%) | aa (%) |
| CaCV | 81.3 | 90.9 | 77.8 | 100 | 93.8 | 100 |
| PBNV | 84.9 | 100 | 85.0 | 100 | 81.3 | 100 |
| MYSV | 81.3 | 100 | 79.6 | 100 | 81.8 | 100 |
| TSWV | 84.9 | 81.8 | 78.8 | 88.9 | 83.9 | 90.9 |
| INSV | 78.1 | 81.8 | 83.0 | 94.4 | 86.2 | 90.9 |

An embodiment of the present invention is disclosed. A tospoviral nucleic acid molecule being used in the embodiment corresponds to an RdRp conserved region [nt (nucleotide) 3975-4928, in accordance with GenBank Accession No. AF133128] in the vc strand of WSMoV L RNA. At least one fragment is made from the tospoviral nucleic acid molecule. At least one modification may be made to the at least one fragment. The modification may allow the addition of a termination codon following a promoter or a leader sequence; may allow a single nucleotide deletion for frame shift; and may allow the at least one fragment being constructed into an inverted repeat structure, wherein the inverted repeat structure has two palindromically linked complementary sequences and may further have an linking sequence between the two complementary sequences. A transgene is made from the at least one fragment. The transgene is introduced into a plant to generate a transgenic plant. The transgenic plant is cultured. A transgenic plant with broad-spectrum resistance is selected and obtained. The transgene may be introduced by biological techniques. For example, the transgene may be constructed into a vector suitable for *Agrobacterium*-mediated transformation.

In the embodiment, the plant is a tobacco plant, *Nicotiana benthamiana*, being a tospoviral host plant. By introducing the transgene into multiple plants, multiple transgenic plant lines are obtained. From each transgenic plant line, multiple transgenic plants may be derived. These transgenic plants are challenged with WSMoV, TSW, GRSV, INSV and PCFV. The transgenic plants that demonstrate a broad-spectrum resistance are screened and selected. A transgenic plant with a broad-spectrum resistance is obtained. The broad-spectrum resistance is not only against the homologous WSMoV but also against heterologous unrelated tospoviruses including TSWV, GRSV, INSV and PCFV. Other than tobacco plants, tomatoes, peppers, cucumbers, melons, watermelons and other crops may also be employed to generate transgenic crops with the present invention to provide broad-spectrum resistance against multiple tospoviruses to control agricultural sufferings caused thereby.

ABBREVIATIONS

CCSV: Calla lily chlorotic spot virus
GRSV: Groundnut ringspot virus
INSV: Impatiens necrotic spot virus
PCFV: Peanut chlorotic fan-spot virus
PBNV: Peanut bud necrosis virus
RdRp: RNA-dependent RNA polymerase
RT-PCR: Reverse transcription-polymerase chain reaction
ssRNA: single-stranded ribonucleic acid
TSWV: Tomato spotted wilt virus
TYRV: Tomato yellow ring virus
WSMoV: Watermelon silver mottle virus

DEFINITIONS

As used herein, the term "broad-spectrum resistance" refers to the resistance expressed by a transgenic plant against tospovirus species homologous or heterologous to the tospovirus from which the transgene is derived. For example, a tospoviral host plant is described to express "broad-spectrum resistance" if the plant is resistant to multiple tospovirus species homologous (WSMoV) or heterologous (TSW, GRSV, INSV, PCFV) to the tospovirus species (WSMoV) from which the transgene is derived.

"Cloning" refers to the process of making a clone, a genetically identical copy. For example, when a fragment of a certain DNA sequence is amplified by PCR and than integrated into a plasmid, the process is described as "cloning" the fragment from the DNA sequence into the plasmid.

A "conserved region of RNA-dependent RNA polymerase" is a region containing five RdRp conserved motifs found among several tospoviruses and may also be referred to as an "RdRp conserved region". The "conserved region of RNA-dependent RNA polymerase of WSMoV" is a region of the vc strand of WSMoV L RNA corresponding to the "conserved region of RNA-dependent RNA polymerase", wherein the region is nt 3975-4928 in accordance with GenBank Accession No. AF133128 and may also be referred to as an "RdRp conserved region of WSMoV".

The term "inoculating" refers to implanting a pathogen in an organism to produce a disease or to stimulate disease resistance.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The phrase "resistant transgenic plant" refers to a plant containing a transgene or transgenes that displays resistance against pathogen of the plant.

"Subcloning" refers the process of making a clone, a genetically identical copy of a cloned biological material.

The term "transgene" refers to the genetic material transferred into a host organism.

A "vector" is an agent that acts as a carrier or transporter. For example, a plasmid that conveys a genetically engineered biological material into a host organism is referred to as a vector.

EXAMPLES

Example 1

Obtaining a DNA Fragment Corresponding to the RdRp Conserved Region of WSMoV (1) Total RNA was isolated from leaves of a WSMoV-infected tobacco plant (*Nicotiana benthamiana*) by ULTRASPEC™ RNA Isolation System (Biotex laboratories, Houston, Tex.).

(2) The primer pair: WL3975(NcoI) (5'-g ccatggagcacacataagcatatcgcc-3') (SEQ ID NO: 1) and WL4928c(SacI) (5'-gagctcgagtcgttctcttctcctggcagc-3') (SEQ ID NO:2) reflects the nt 3975-3998 and the nt 4907-4928 regions of the vc strand of WSMoV L RNA in accordance with GenBank Accession No. AF133128 with an NcoI site and a SacI site (underlined), respectively. The sequence of the nt 3975-4928 region of the vc strand of WSMoV L RNA in accordance with GenBank Accession No. AF133128 is: "gagcacacataagcatatcgc-
ccaatctgatccttctgaggcaatatctatatctggagattacaaaataaaga act-
tagcatcactgtcatatgatactataac-
taactataacacagcacttcaaaagaacctggaatgtaaaatggctt
tcttgtcggcagatcaatcaaagtg-
gtctgcatcagataactacaaatacatactagctgttataatgaaccctat attgac-
cactggagagataaacttgatgtgt-
gaatgcataatgatgtatataaagttaaagagggtgtgcatcccta
ctgatatattcctaaaccttaaaagag-
gtcaaacagagtacgggtcttatgggactgctttatctgtattgacagata atttg-
gaaacaaacacattcccagtgtctat-
gaactggctacaagggaatctcaattatatcatctgtctaccattct
tgtgccatgataggttatgaaaaag-
caatgaaaaagatgaaagattatgattacaataagatggatggtacactct gat-
gataatgctacatctatagtagtcagag-
gagacttaaagaaacttttgtccagctttaactgttctagtctgtctga
attgctgttccggagtattcagtcacat-
taaaagttactgtataacactgaacccctaagaaaagttatgcatcagaa tctgaagt-
tgaattcatatcagaaagaattat-
taatggtgctgtgatacctctgtactgtaggcatggccaactgca
gcacagaaagctctcataaatagt-
tattttgacgatttgatgtctctttctattcatattacaatgcttttaagaaagggttg
ccccaatgaattgataccatttgcttat-
gcagcaatacaagttcagtcacttagcatatattcaatgctgccaggaga
agagaacgac" (SEQ ID NO:3), and a full complement of the nt 3975-4928 region of the vc strand of WSMoV L RNA in accordance with GenBank Accession No. AF133128 is:

"gtcgttctcttctcctggcagcattgaatatatgctaagtgactgaact tgtattgctgcataagcaaatggtatcaattcattggggcaacccttct taaaagcattgtaatatgaatagaaagagacatcaaatcgtcaaaataac tattatgagagctttctgtgctgcagttggccaaatgcctacagtacaga ggtatcacagcaccattaataattctttctgatatgaattcaacttcaga ttctgatgcataactttcttagggttcagtgttatacagtaactttaa aatgtgactgaatactccggaacagcaattcagacagactagaacagtta aagctggacaaaagtttctttaagtctcctctgactactatagatgtagc attatcatcagagtgtaccatccatcttattgtaaaatcataatctttca tcttttcattgcttttcataacctatcatggcacaagaatggtagaca gatgataaataattgagattcccttgtagccagttcatagacactgggaa tgtgtttgtttccaaattatctgtcaatacagataaagcagtcccataag acccgtactctgtttgacctcttttaaggtttaggaatatatcagtaggg atgcacaccctcttttaactttatatacatcattatgcattcacacatcaa gtttatctctccagtggtcaatataggggttcattataacagctagtatgt atttgtaggttaaatctgatgcagaccactttgattgatctgccgacaag aaagccattttacattccaggttcttttgaagtgctgtgttatagttagt tatagtatcatatgacagtgatgctaagttctttattttgtaatctccag atatagatattgcctcagaaggatcagattgggcgatatgcttgtatgtg tgctc."

(3) The conserved region containing five RdRp motifs of WSMoV was amplified by RT-PCR with the primer pair: WL3975(NcoI) and WL4928c(SacI). With reverse transcriptase applied in RT, the first strand cDNA was generated. The fragment of the RdRp conserved region was then amplified with Taq DNA polymerase applied in PCR. The expected length of the amplified fragment was 954 bp (base pairs) and was visualized under uv (ultraviolet) by electrophoresis in 1.2% agarose gels with EtBr (ethidium bromide) staining. The amplified fragment was named as the WLm fragment. The sequence of the WLm fragment is:

(SEQ ID NO: 4.)
"gccatggagcacacataagcatatcgcccaatctgatccttctgagg caatatctatatctggagattacaaaataaagaacttagcatcactgtca tatgatactataactaactataacacagcacttcaaaagaacctggaatg taaaatggctttcttgtcggcagatcaatcaaagtggtctgcatcagatt taacctacaaatacatactagctgttataatgaaccctatattgaccact ggagagataaacttgatgtgtgaatgcataatgatgtatataaagttaaa gagggtgtgcatccctactgatatattcctaaaccttaaaagaggtcaaa cagagtacgggtcttatgggactgctttatctgtattgacagataatttg gaaacaaacacattcccagtgtctatgaactggctacaagggaatctcaa ttatttcatctgtctaccattcttgtgccatgataggttatgaaaaag caatgaaaaagatgaaagattatgatttacaataagatggatggtacac tctgatgataatgctacatctatagtagtcagaggagacttaaagaaact tttgtccagctttaactgttctagtctgtctgaattgctgttccggagta -continued
```
ttcagtcacattttaaaagttactgtataacactgaaccctaagaaaagt tatgcatcagaatctgaagttgaattcatatcagaaagaattattaatgg tgctgtgatacctctgtactgtaggcatttggccaactgcagcacagaaa gctctcataatagttattttgacgatttgatgtctctttctattcatatt acaatgcttttaagaaagggttgccccaatgaattgataccatttgctta tgcagcaatacaagttcagtcacttagcatatattcaatgctgccaggag aagagaacga<u>ctcgag</u>ctc"
```

(4) The WLm fragment was cloned by TOPO TA Cloning Kit (Invitrogen, Carlsbad, Calif.) to confirm the sequence and was used as the template for further constructions. The DNA sequence of the cloned fragment was sequenced by ABI377-19 automatic DNA sequencing system (Perkin-Elmer Applied Biosystems, Foster City, Calif.). The DNA sequence was subjected to the BESTFIT program of the GCG software package (Wisconsin Package version 9.0, Genetics Computer Group, Madison, Wis.) to validate the fidelity of the cloned fragment.

Example 2

Construction of Translatable and Nontranslatable Transgenes (1) Method

The L RNA of WSMoV is of negative polarity and the vc strand of L RNA, as a protein expression template, encodes putative RdRp. Thus, a DNA fragment amplified from a vc strand RNA template is transcribed into a translatable RNA transcript. On the contrary, a DNA fragment amplified from a v strand RNA template is transcribed into a nontranslatable RNA transcript. A nontranslatable RNA transcript may also be generated by adding at least one stop codon in the 5'-end or by deleting a single nucleotide to induce frame shift in the transcript.

(2) Translatable Fragment

With reference to FIG. 1, The WLm fragment carried the nt 3975-4928 region of WSMoV L RNA vc strand in accordance with GenBank Accession No. AF133128. The fragment encoded five RdRp motifs and was translatable. The translated amino acid sequence of the WLm fragment is:

```
                                              (SEQ ID NO: 5.)
"MEHTYKHIAQSDPSEAISISGDYKIKNLASLSYDTITNYNTALQKNLEC

KMAFLSADQSKWSASDLTYKYILAVIMNPILTTGEINLMCECIMMYIKL

KRVCIPTDIFLNLKRGQTEYGSYGTALSVLTDNLETNTFPVSMNWLQGN

LNYLSSVYHSCAMIGYEKAMKKMKDYDFTIRWMVHSDDNATSIVVRG

DLKKLLSSFNCSSLSELLFRSIQSHFKSYCITLNPKKSYASESEVEFISE

RIINGAVIPLYCRHLANCSTESSHNSYFDDLMSLSIHITMLLRKGCPNEL

IPFAYAAIQVQSLSIYSMLPGEENDSS"
```

(3) Designation of Primers: WLt3975(NcoI) and WLst3975(NcoI)

Using the RdRp conserved region of WSMoV as a template, the following primers were designed: WLt3975(NcoI) (5'-<u>gccatgg</u>aataggagcacacatacaagcatatcgcc-3') (SEQ ID NO:6) and WLst3975(NcoI): (5'-g<u>ccatgg</u>ataataggagcacacatacaagcatatcgcc-3') (SEQ ID NO:7).

Two in-frame stop codons were inserted at the 5'-end of WLt3975(NcoI). An in-frame stop codon and a −1 frameshift stop codon were inserted at the 5'-end of WLst3975 (NcoI). The stop codon (taatag) was italicized. A single nucleotide deletion was performed between the NcoI site and the stop codons on the 5'-end of WLst3975(NcoI).

(4) Nontranslatable Fragments

A fragment was amplified from the cloned RdRp conserved region of WSMoV with the primer set: WLt3975 (NcoI) and WL4928c(SacI) using PCR and TA cloning techniques. The stop codons located at the 5'-end made the fragment nontranslatable. The amplified fragment is named as the WLmt fragment.

The sequence of the WLmt fragment is:

```
                                              (SEQ ID NO: 8.)
"g<u>ccatgg</u>aa*taatag*gagcacacatacaagcatatcgcccaatctgatc cttctgaggcaatatctatatctggagattacaaaataaagaacttagca tcactgtcatatgatactataactaactataacacagcacttcaaaagaa cctggaatgtaaaatggctttcttgtcggcagatcaatcaaagtggtctg catcagatttaacctacaaatacatactagctgttataatgaaccctata ttgaccactggagagataaacttgatgtgtgaatgcataatgatgtatat aaagttaaagagggtgtgcatccctactgatatattcctaaaccttaaaa gaggtcaaacagagtacgggtcttatgggactgctttatctgtattgaca gataatttggaaacaaacacattcccagtgtctatgaactggctacaagg gaatctcaattatttatcatctgtctaccattcttgtgccatgataggtt atgaaaaagcaatgaaaaagatgaaagattatgattttacaataagatgg atggtacactctgatgataatgctacatctatagtagtcagaggagactt aaagaaacttttgtccagctttaacttgttctagtctgtctgaattgctgt tccggagtattcagtcacattttaaaagttactgtataacactgaaccct aagaaaagttatgcatcagaatctgaagttgaattcatatcagaaagaat tattaatggtgctgtgatacctctgtactgtaggcatttggccaactgca gcacagaaagctctcataatagttattttgacgatttgatgtctctttct attcatattacaatgcttttaagaaagggttgccccaatgaattgatacc atttgcttatgcagcaatacaagttcagtcacttagcatatattcaatgc tgccaggagaagagaacga<u>ctcgag</u>ctc"
```

On the other hand, another fragment was amplified from the cloned RdRp conserved region of WSMoV with the primer set: WLst3975(NcoI) and WL4928c(SacI) using PCR and TA cloning techniques. Not only the stop codons located at the 5'-end but also the frame shift caused by the single nucleotide deletion made the fragment nontranslatable. The amplified fragment is named as the WLmts fragment. The sequence of the WLmts fragment is:

```
                                              (SEQ ID NO: 9.)
"g<u>ccatgg</u>a*taatag*gagcacacatacaagcatatcgcccaatctgatcc ttctgaggcaatatctatatctggagattacaaaataaagaacttagcat cactgtcatatgatactataactaactataacacagcacttcaaaagaac ctggaatgtaaaatggctttcttgtcggcagatcaatcaaagtggtctgc
```

-continued
```
atcagatttaacctacaaatacatactagctgttataatgaaccctatat tgaccactggagagataaacttgatgtgtgaatgcataatgatgtatata aagttaaagagggtgtgcatccctactgatatattcctaaaccttaaaag aggtcaaacagagtacgggtcttatgggactgctttatctgtattgacag ataatttggaaacaaacacattcccagtgtctatgaactggctacaaggg aatctcaattatttatcatctgtctaccattcttgtgccatgataggtta tgaaaaagcaatgaaaaagatgaaagattatgattttacaataagatgga tggtacactctgatgataatgctacatctatagtagtcagaggagactta aagaaacttttgtccagctttaactgttctagtctgtctgaattgctgtt ccggagtattcagtcacattttaaaagttactgtataacactgaaccta agaaaagttatgcatcagaatctgaagttgaattcatatcagaaagaatt attaatggtgctgtgatacctctgtactgtaggcatttggccaactgcag cacagaaagctctcataatagttattttgacgatttgatgtctctttcta ttcatattacaatgcttttaagaaaggggttgccccaatgaattgatacca tttgcttatgcagcaatacaagttcagtcacttagcatatattcaatgct gccaggagaagagaacgactcgagctc"
```

(5) Designation of Primers: WL4928c(NcoI) and WL3975 (SacI)

Using the RdRp conserved region of WSMoV as a template, the following primers were designed: WL4928c(NcoI) (5-ccatgggtcgttctcttctcctggcagc-3') (SEQ ID NO: 10) and WL3975(SacI) (5'-gagctcgagcacacatacaagcatatcgcc-3') (SEQ ID NO:11). Note that the restriction sites of WL4928c (NcoI) and WL3975(SacI) are different from those of WL3975(NcoI) and WL4928c(SacI).

(6) Antisense Nontranslatable Fragment

The fragment amplified with WL4928c(NcoI) and WL3975(SacI) is named as the WLmAs fragment, and has opposite cloning sites (restriction sites NcoI and SacI) comparing with the WLm fragment amplified with WL3975 (NcoI) and WL4928c(SacI). The WLmAs fragment is suitable for making an antisense transgene. The sequence of the WLmAs fragment is:

```
                                    (SEQ ID NO: 12.)
"ccatgggtcgttctcttctcctggcagcattgaatatatgctaagtgac tgaacttgtattgctgcataagcaaatggtatcaattcattggggcaacc cttcttaaaagcattgtaatatgaatagaaagagacatcaaatcgtcaa aataactattatgagagctttctgtgctgcagttggccaaatgcctacag tacagaggtatcacagcaccattaataattctttctgatatgaattcaac ttcagattctgatgcataactttttcttagggttcagtgttatacagtaac ttttaaaatgtgactgaatactccggaacagcaattcagacagactagaa cagttaaagctggacaaaagtttctttaagtctcctctgactactataga tgtagcattatcatcagagtgtaccatccatcttattgtaaaatcataat ctttcatcttttcattgcttttcataacctatcatggcacaagaatgg tagacagatgataaataattgagattcccttgtagccagttcatagacac tgggaatgtgtttgtttccaaattatctgtcaatacagatacagcagtcc
```

-continued
```
cataagacccgtactctgtttgacctcttttaaggtttaggaatatatca gtagggatgcacaccctctttaactttatatacatcattatgcattcaca catcaagtttatctctccagtggtcaatatagggttcattataacagcta gtatgtatttgtaggttaaatctgatgcagaccactttgattgatctgcc gacaagaaagccattttacattccaggttcttttgaagtgctgtgttata gttagttatagtatcatatgacagtgatgctaagttctttattttgtaat ctccagatatagatattgcctcagaaggatcagattgggcgatatgcttg tatgtgtgctcgagctc"
```

(7) Confirmation of the Sequences and Addition of the β-Glucuronidase (GUS) Gene Leader Sequence The WLm, WLmt, WLmts and WLmAs fragments were all cloned with a TOPO TA Cloning Kit (Invitrogen) for sequencing, and then released from plasmids by NcoI and SacI digestion. Subsequently, each cloned fragment was subcloned into a GUS gene-carrying pGEM-7zf(+) vector (Promega, Madison, Wis.) to obtain the GUS leader sequence.

(8) Construction of pBGWLm, pBGWLmt, pBGWLmts and pBGWLmAs Vectors Containing Each Transgene.

A binary vector pBI121 (Clontech, Mountain View, Calif.) comprising a selection-marker, neomycin phosphotransferase (nptII) gene, was used in the construction of pBG-WLm, pBGWLmt, pBGWLmts and pBGWLmAs vectors.

The individual subcloned fragments containing the GUS leader sequence were cloned in the binary vector pBI121 with a Cauliflower mosaic virus (CaMV) 35S promoter and a NOS terminator via XbaI and SacI sites.

The resulted vectors containing the WLm, WLmt, WLmts and WLmAs fragments were then named as pBGWLm, pBG-WLmt, pBGWLmts and pBGWLmAs, respectively.

Example 3

Construction of Inverted Repeat Transgene (1) Construction of the WLm-Linker Fragment The primers: WL4928c(XbaI) (5'-atgc tctagagtcgttctcttctcctggcagc-3') (SEQ ID NO:13) and WL3975Nco-linker (5'-ccgg ccatggagagcaatgagcacacatacaagca-3') (SEQ ID NO: 14) were designed.

A fragment was amplified with WL4928c(XbaI) and WL3975Nco-linker from the RdRp conserved region of WSMoV and named as the WLm-linker fragment. The WLm-linker fragment had an XbaI restriction site (underlined) and an NcoI restriction site (underlined) as well as a linker sequence (sometimes referred to as "spacer") which were italicized (agagcaat). The sequence of the WLm-linker fragment is:

```
                                    (SEQ ID NO: 15.)
"atgctctagagtcgttctcttctcctggcagcattgaatatatgctaag tgactgaacttgtattgctgcataagcaaatggtatcaattcattgggc aaccctttcttaaaagcattgtaatatgaatagaaagagacatcaaatcg tcaaaataactattatgagagctttctgtgctgcagttggccaaatgcct
```

-continued
```
acagtacagaggtatcacagcaccattaataattctttctgatatgaatt caacttcagattctgatgcataacttttcttagggttcagtgttatacag taacttttaaaatgtgactgaatactccggaacagcaattcagacagact agaacagttaaagctggacaaaagtttctttaagtctcctctgactacta tagatgtagcattatcatcagagtgtaccatccatcttattgtaaaatca taatctttcatcttttcattgcttttcataacctatcatggcacaaga atggtagacagatgataaataattgagattcccttgtagccagttcatag acactgggaatgtgtttgtttccaaattatctgtcaatacagataaagca gtcccataagacccgtactctgtttgacctcttttaaggtttaggaatat atcagtagggatgcacaccctcttaactttatacatcattatgcatt cacacatcaagtttatctctccagtggtcaatatagggttcattataaca gctagtatgtatttgtaggttaaatctgatgcagaccactttgattgatc tgccgacaagaaagccattttacattccaggttcttttgaagtgctgtgt tatagttagttatagtatcatatgacagtgatgctaagttctttattttg taatctccagatatagatattgcctcagaaggatcagattgggcgatatg cttgtatgtgtgctcattgctctccatggccgg"
```

(2) Construction of the pBWLmds Vector

The WLm-linker fragment was cloned by TOPO TA Cloning Kit (Invitrogen) to confirm sequence. With reference to FIG. 1, the XbaI/NcoI-digested WLm-linker fragment and the NcoI/SacI-digested WLm fragment were mixed with XbaI/SacI-digested pBI121 for direct ligation for generating an inverted repeat transgene in pBWLmds. In the vector pBWLmds, the WLm-linker fragment and the WLm fragment were combined with an NcoI site and the combined fragment is named as the WLmds fragment. The sequence of WLmds fragment is:

```
                                          (SEQ ID NO: 16.)
"atgctctagagtcgttctcttctcctggcagcattgaatatatgctaag tgactgaacttgtattgctgcataagcaaatggtatcaattcattgggc aacccttcttaaaagcattgtaatatgaatagaaagagacatcaaatcg tcaaaataactattatgagagctttctgtgctgcagttggccaaatgcct acagtacagaggtatcacagcaccattaataattctttctgatatgaatt caacttcagattctgatgcataacttttcttagggttcagtgttatacag taacttttaaaatgtgactgaatactccggaacagcaattcagacagact agaacagttaaagctggacaaaagtttctttaagtctcctctgactacta tagatgtagcattatcatcagagtgtaccatccatcttattgtaaaatca taatctttcatcttttcattgcttttcataacctatcatggcacaaga atggtagacagatgataaataattgagattcccttgtagccagttcatag acactgggaatgtgtttgtttccaaattatctgtcaatacagataaagca gtcccataagacccgtactctgtttgacctcttttaaggtttaggaatat atcagtagggatgcacaccctcttaactttatacatcattatgcatt cacacatcaagtttatctctccagtggtcaatatagggttcattataaca gctagtatgtatttgtaggttaaatctgatgcagaccactttgattgatc tgccgacaagaaagccattttacattccaggttcttttgaagtgctgtgt tatagttagttatagtatcatatgacagtgatgctaagttctttattttg taatctccagatatagatattgcctcagaaggatcagattgggcgatatg cttgtatgtgtgctcattgctctccatggagcacacatacaagcatatcg cccaatctgatccttctgaggcaatatctatatctggagattacaaaata aagaacttagcatcactgtcatatgatactataactaactataacacagc acttcaaaagaacctggaatgtaaaatggcttcttgtcggcagatcaat caaagtggtctgcatcagatttaacctacaaatacatactagctgttata atgaaccctatattgaccactggagagataaacttgatgtgtgaatgcat aatgatgtatataaagttaaagagggtgtgcatccctactgatatattcc taaaccttaaaagaggtcaaacagagtacgggtcttatgggactgcttta tctgtattgacagataatttggaaacaaacacattcccagtgtctatgaa ctggctacaagggaatctcaattatttatcatctgtctaccattcttgtg ccatgataggttatgaaaaagcaatgaaaaagatgaaagattatgatttt acaataagatggatggtacactctgatgataatgctacatctatagtagt cagaggagacttaaagaaacttttgtccagctttaactgttctagtctgt ctgaattgctgttccggagtattcagtcacattttaaaagttactgtata acactgaaccctaagaaaagttatgcatcagaatctgaagttgaattcat atcagaaagaattattaatggtgctgtgatacctctgtactgtaggcatt tggccaactgcagcacagaaagctctcataatagttattttgacgatttg atgtctctttctattcatattacaatgcttttaagaaagggttgccccaa tgaattgataccatttgcttatgcagcaatacaagttcagtcacttagca tatattcaatgctgccaggagaagagaacgactcgagctc"
```

As described above, the WLmds fragment has the WLm-linker fragment and the WLm fragment. The WLm-linker fragment reflected WSMoV L RNA v strand of the RdRp conserved region, while the WLm fragment reflected the vc strand of the RdRp conserved region. With the help of the linker sequence located near the 3'-end of the WLm-linker fragment, the transcript of the WLmds fragment was expected to be transcribed to a double-stranded (ds) RNA in vivo.

Example 4

Culture of Transgenic Plants

Plasmids pBGWLm, pBGWLmt, pBGWLmts, pBGWL-mAs and pBWLmds, were used as vectors to transfer individual transgene constructs into plants. They were transferred into an *Agrobacterium tumefaciens* disarmed strain LBA 4404 by direct transformation with liquid nitrogen treatment.

The leaf-disk transformation method was performed to separately introduce the individual transgenes into cells of *Nicotiana benthamiana* by Agrobacterium-mediated transformation as described. The transformed cells were selected on MS104 selection medium containing MS salts (Gibco BRL, Gaithersburg, Md.), 0.1% B5 vitamins, 3% sucrose, 1 μg/ml 6-benzylamino purine (BA), 0.1 μg/ml naphthaleneacetic acid (NAA), 0.8% agar, 500 μg/ml carbenicillin and 200 μg/ml kanamycin. Developed shoots were excised and cultured on the hormone-free medium (MS medium containing 200 μg/ml kanamycin) for rooting. Rooted shoots were transplanted in vermiculite soil and kept under greenhouse conditions for further analyses.

Thus, multiple transgenic tobacco plant lines were obtained from each of the transgenes, and multiple transgenic plants of each transgenic plant line were derived and cultured. Each of the transgenic plant lines was named after the fragment used to construct the transgene. Transgenic plant lines transformed with vectors pBGWLm, pBGWLmt, pBGWLmts, pBGWLmAs or pBWLmds were named as WLm, WLmt, WLmts, WLmAs and WLmds lines, respectively. Individual transgenic plants multiplied from a transgenic plant line, which was established from a single regenerated shoot, were named after the line and numbered. Transgenic plants further derived from the individual transgenic plants of each transgenic line carried the same name and number.

Example 5

Confirmation of Transgenic Tobacco Plant Lines (1) Total genomic DNAs were extracted from leaves of untransformed or transgenic tobacco plants with Genomic DNA Purification Kit (GeneMark, Taichung, Taiwan), according to the manufacturer's instructions.

(2) The primer set: WL3975(NcoI)/WL4928c(SacI) was used to confirm the existence of transgenes. In addition, the primer pair: PNPTII (5'-atgattgaacaagatggattgcac-3') (SEQ ID NO: 17) and MNPTII (5'-gaagaactcgtcaagaaggcgata-3') (SEQ ID NO: 18) was used to amplify the selection-marker neomycin phosphotransferase (nptII) gene linked with the transgenes.

Fifty nanograms of extracted DNAs were used as templates, and PCR was conducted adopting the thermal profile: 1 min for denaturation at 94° C., 2 min for annealing at 58° C., and 3 min for synthesis at 72° C. for 34 cycles, followed by a final extended synthesis at 72° C. for 7 min. PCR products were analyzed by electrophoresis in 1% agarose gel.

Example 6

Screening and Analysis of Viral Resistance (1) Virus Inocula
Virus Sources
WSMoV and PCFV were collected from watermelon and peanut, respectively, in Taiwan.

The New York isolate of TSWV (TSWV-NY) isolated from tomato was provided by R. Provvidenti, New York State Experiment Station, Geneva.

GRSV collected from tomato in Brazil was obtained from D. Gonsalves, New York State Experiment Agricultural Station.

An isolate of INSV (INSV-M) collected from impatiens in the United States was provided by J. Moyer, North Carolina State University, Raleigh.

All viruses were maintained in a local lesion host: *Chenopodium quinoa* Willd., and a systemic host: *Nicotiana benthamiana* Domin.

Inoculation

Transgenic tobacco plant lines transformed with the vectors containing a translatable transgene (pBGWLm), a non-translatable transgene (pBGWLmt, pBGWLmts or pBGWLmAs) or an inverted repeat transgene (pBWLmds) were inoculated with WSMoV or other serologically unrelated tospoviruses (TSWV, GRSV, INSV, and PCFV). Each of the inocula for individual tospoviruses listed above was prepared as a suspension from leaves of virus-infected tobacco (*N. benthamiana*) plants. The leaves were ground in 10 mM potassium phosphate buffer (pH 7.0) containing 10 mM sodium sulfite. The inoculations were performed by mechanically introducing the inocula onto the two youngest fully expanded leaves of a transgenic tobacco plant. In this example, the viral inoculations were performed by rubbing the leaves of transgenic tobacco plants with the inocula to evaluate transgenic resistance under greenhouse conditions.

In addition, the symptomatic untransformed or transgenic tobacco plants challenged with individual tospoviruses were confirmed by indirect enzyme-linked immunosorbent assay (ELISA) using the antisera against the N protein of WSMoV, TSWV, GRSV, INSV or PCFV at a 1/4000 dilution.

(2) Evaluation of Transgenic Resistance

The phenomena of tospovirus-challenged transgenic tobacco plants were defined as follows:

(a) if typical symptoms developed on systemic leaves of the infected transgenic plants were the same as those caused on untransformed plants 4-7 days post-inoculation (dpi), the transgenic plants were considered as susceptible (S) to the challenging virus;

(b) if the virus-infected transgenic plants showed symptoms 7 days later than untransformed plants did, the transgenic plants were regarded as moderately resistant (MR) against the challenging virus; and (c) if all the transgenic plants showed no symptoms of virus infection 28 dpi, the transgenic plants were classified as highly resistant (HR) against the challenging virus.

Within each line, all tested transgenic plants showing uniform response to the same virus were verified. A transgenic line identified as MR or HR was also identified as a resistant (R) line against the challenging virus.

(3) Inoculation with WSMoV

Untransformed and transgenic tobacco plants were first inoculated with WSMoV to evaluate the resistance under temperature controlled (28° C.) greenhouse conditions. Five plants of each transgenic line were inoculated with the virus. The resistant lines were confirmed with two challenges.

The phenomena of WSMoV-challenged transgenic tobacco lines were summarized in Table 2.

TABLE 2

Evaluation of transgenic tobacco lines by inoculation with WSMoV.

| Vector | Total assayed lines | Challenged with WSMoV | | |
|---|---|---|---|---|
| | | Total R lines (%) | HR (%) | MR (%) |
| pBGWLm | 30 | 14 (46.7) | 10 (33.3) | 4 (13.3) |
| pBGWLmt | 30 | 19 (63.3) | 12 (40.0) | 7 (23.3) |
| pBGWLmts | 30 | 19 (63.3) | 12 (40.0) | 7 (23.3) |
| pBGWLmAs | 30 | 20 (66.7) | 11 (36.7) | 9 (30.0) |
| pBWLmds | 30 | 21 (70.0) | 9 (30.0) | 12 (40.0) |

Four weeks after mechanical inoculation with WSMoV, 14 out of 30 WLm lines (46.7%), 19 out of 30 WLmt lines (63.3%), 19 out of 30 WLmts lines (63.3%), 20 out of 30 WLmAs lines (66.7%), and 21 out of 30 WLmds lines (70.0%) showed resistance against WSMoV. Indeed, 30.0%-40.0% of resistant lines were immune to WSMoV infection, such as 10 WLm lines (33.3%), 12 WLmt lines (40.0%), 12 WLmts lines (40.0%), 11 WLmAs lines (36.7%) and 9 WLmds lines (30.0%); and 13.3%-40.0% of resistant lines showed delayed symptoms after challenged with WSMoV, such as 4 WLm lines (13.3%), 7 WLmt lines (23.3%), 7 WLmts lines (23.3%), 9 WLmAs lines (30.0%) and 12 WLmds lines (40.0%).

These results indicated that the RdRp conserved region-corresponding sequence of WSMoV L RNA was able to build up resistance against WSMoV in transgenic tobacco plants. The vectors containing nontranslatable transgenes, including pBGWLmt, pBGWLmts, pBGWLmAs and pBWLmds, whatever the transgene constructs were sense, antisense or inverted repeat, they were able to significantly increase the WSMoV protection efficiency (63.3% to 70.0%) than the translatable transgene WLm (46.7%).

(4) Inoculation with TSWV, GRSV, INSV or PCFV

TSWV, GRSV, INSV and PCFV are heterologous species from WSMoV, they belong to serogroups or serotypes different from WSMoV. To evaluate the broad-spectrum resistance, the WSMoV-resistant transgenic tobacco lines were further challenged with TSW, GRSV, INSV or PCFV under the same greenhouse conditions. Five plants of each transgenic line were inoculated with individual viruses. The resistant lines were confirmed with two challenges.

Results of the broad-spectrum resistance to these four tospovirus species were showed in Table 3. The data were taken at 4 weeks after inoculation.

TSWV, GRSV, INSV and PCFV at the same time. WLm-11 was MR to WSMoV, TSWV, GRSV and PCFV, and HR to INSV. WLm-30 was HR to WSMoV, GRSV and PCFV, and MR to TSWV and INSV.

In 19 WSMoV-resistant WLmt lines, 10 lines (52.6%), 10 lines (52.6%), 11 lines (57.9%) and 14 lines (73.7%) showed resistance to TSW, GRSV, INSV and PCFV, respectively. Out of 6 lines (31.6%) and 4 lines (21.1%) were MR and HR to TSWV or GRSV, respectively; out of 6 lines (31.6%) and 5 lines (26.3%) were MR and HR to INSV, respectively; and out of 7 lines (36.8%) and 7 lines (36.8%) were MR and HR to PCFV, respectively. Six lines, WLmt-4, 5, 7, 9, 13 and 17, were resistant to all five challenged tospoviruses with divergent resistances. Indeed, two of them, WLmt-4 and WLmt-13, were immune to all challenged tospoviruses.

In 19 WSMoV-resistant WLmts lines, 11 lines (57.9%), 13 lines (68.4%), 13 lines (68.4%) and 19 lines (100.0%) showed resistance to TSWN, GRSV, INSV and PCFV, respectively. Out of 4 lines (21.1%) and 7 lines (36.8%) were MR and HR to TSW, respectively; out of 9 lines (47.4%) and 4 lines (21.1%) were MR and HR to GRSV; out of 6 lines (31.6%) and 7 lines (36.8%) were MR and HR to INSV, respectively; and out of 10 lines (52.6%) and 9 lines (47.4%) were MR and HR to PCFV, respectively. Seven lines, WLmts-2, 5, 7, 10, 13,

TABLE 3

Evaluation of transgenic tobacco lines with tospovirus species unrelated to WSMoV

| Vector | Total assayed lines | Total R lines (%) | HR (%) | MR (%) | Total R lines (%) | HR (%) | MR (%) |
|---|---|---|---|---|---|---|---|
| | | Challenged with TSWV | | | Challenged with GRSV | | |
| pBGWLm | 14 | 6 (42.9) | 0 (0) | 6 (42.9) | 7 (50.0) | 2 (14.3) | 5 (35.7) |
| pBGWLmt | 19 | 10 (52.6) | 4 (21.1) | 6 (31.6) | 10 (52.6) | 4 (21.1) | 6 (31.6) |
| pBGWLmts | 19 | 11 (57.9) | 7 (36.8) | 4 (21.1) | 13 (68.4) | 4 (21.1) | 9 (47.4) |
| pBGWLmAs | 20 | 10 (50.0) | 5 (25.0) | 5 (25.0) | 11 (55.0) | 6 (30.0) | 5 (25.0) |
| pBWLmds | 21 | 15 (71.4) | 6 (28.6) | 9 (42.9) | 15 (71.4) | 2 (9.5) | 13 (61.9) |
| | | Challenged with INSV | | | Challenged with PCFV | | |
| pBGWLm | 14 | 5 (35.7) | 2 (14.3) | 3 (21.4) | 10 (71.4) | 4 (28.6) | 6 (42.9) |
| pBGWLmt | 19 | 11 (57.9) | 5 (26.3) | 6 (31.6) | 14 (73.7) | 7 (36.8) | 7 (36.8) |
| pBGWLmts | 19 | 13 (68.4) | 7 (36.8) | 6 (31.6) | 19 (100.0) | 9 (47.4) | 10 (52.6) |
| pBGWLmAs | 20 | 11 (55.0) | 2 (10.0) | 9 (45.0) | 15 (75.0) | 5 (25.0) | 10 (50.0) |
| pBWLmds | 21 | 16 (76.2) | 9 (42.9) | 7 (33.3) | 16 (76.2) | 6 (28.6) | 10 (47.6) |

In 14 WSMoV-resistant WLm lines, 6 lines (42.9%) showed MR but no lines were immune to TSWV. Out of 7 lines (50.0%) resistant to GRSV, 5 were MR lines (35.7%) and 2 HR lines (14.3%). Out of 5 lines (35.7%) showing resistance against INSV, 3 were MR lines (21.4%) and 2 HR lines (14.3%). Out of 10 lines (71.4%) resistant to PCFV, 6 were MR lines (42.9%) and 4 HR lines (28.6%). Except the line WLm-16 which was resistant only to WSMoV, all other WSMoV-resistant lines produced different levels of resistance against additionally one to four tospovirus species. Especially, the lines WLm-11 and WLm-30 were highly resistant to five tospovirus species including WSMoV, 16 and 24, were resistant to all five challenged tospoviruses with different levels of resistance. WLmts-7 was especially immune to all challenged tospoviruses.

In 20 WSMoV-resistant WLmAs lines, 10 lines (50.0%), 11 lines (55.0%), 11 lines (55.0%) and 15 lines (75.0%) showed resistance to TSWV, GRSV, INSV and PCFV, respectively. Out of 5 lines (25.0%) and 5 lines (25.0%) were MR and HR to TSWV, respectively; out of 5 lines (25.0%) and 6 lines (30.0%) were MR and HR to GRSV, respectively; out of 9 lines (45.0%) and 2 lines (10.0%) were MR and HR to INSV, respectively; and out of 10 lines (50.0%) and 5 lines (25.0%) were MR and HR to PCFV, respectively. Five lines, WLmAs-7, 8, 19, 20 and 21, showed different levels of resistance to the five challenged tospoviruses. WLmAs-7 was immune to these challenging viruses.

Moreover, in 21 WSMoV-resistant WLmds lines, 15 lines (71.4%), 15 lines (71.4%), 16 lines (76.2%) and 16 lines (76.2%) showed resistance to TSWV, GRSV, INSV and PCFV, respectively. Out of 9 lines (42.9%) and 6 lines (28.6%) were MR and HR to TSWV, respectively; out of 13 lines (61.9%) and 2 lines (9.5%) were MR and HR to GRSV, respectively; out of 7 lines (33.3%) and 9 lines (42.9%) were MR and HR to INSV, respectively; and out of 10 lines (47.6%) and 6 lines (28.6%) were MR and HR to PCFV, respectively. Seven lines, WLmds-2, 4, 10, 15, 16, 22 and 24, were divergently resistant to all five challenged tospoviruses. However, no lines derived from WLmds were immune to all challenging viruses.

(5) Conclusion on Resistance Screening and Analyses

Over all, transgenic tobacco plant lines obtained by the introduction of pBGWLm, pBGWLmt, pBGWLmts, pBGWLmAs or pBWLmds with different transgenes were able to produce broad-spectrum resistance not only against WSMoV, the viral origin of the transgenes, but also against TSW, GRSV, INSV and PCFV, with delayed symptom development or immune response.

Example 7

Expression Levels of Transgene Transcripts of Resistant Transgenic Tobacco Lines (1) Northern Blotting Twenty to thirty µg of total RNAs were separated in 1.2% agarose gels with formaldehyde, blotted onto Hybond-N nylon membrane (Amersham Biosciences, Buckinghamshire, UK), and hybridized with the α-$^{32}$P-dATP-labeled DNA probe corresponding to the WLm fragment prepared with Primer-It II Random Primer Labeling Kit (Stratagene, La Jolla, Calif.). The results of hybridization were visualized by autoradiography with Kodak BioMax films.

(2) Results

Transgene transcripts in the resistant tobacco lines conferring broad-spectrum resistance were expressed in low levels. Transgene transcripts of the broad-spectrum resistant transgenic tobacco plant lines against five distinct tospovirus species were detected. All assayed resistant lines expressed transcripts in low or undetectable levels. No signals were detected in untransformed tobacco plants. Higher expression levels in two susceptible lines, WLmAs-4 and WLmds-13, were detected. It indicated that the broad-spectrum resistance was mediated by RNA silencing.

Example 8

Analysis of Total Transgene Copy Numbers (1) Southern Blotting

Transgene copy numbers of the broad-spectrum resistant tobacco lines were analyzed by Southern blotting.

Fifteen to twenty µg of genomic DNAs were digested with SspI and separated at 120 V in 0.8% agarose, and then transferred onto Hybond-N nylon membrane (Amersham Biosciences) to hybridize with the α-$^{32}$P-dATP-labeled DNA probe described above. The results of hybridization were detected by autoradiography.

(2) Results

In untransformed tobacco plants, as negative controls, no signals were detected. The transgenic plants of the resistant transgenic tobacco plant lines carry one, two or multiple transgene copies.

CONCLUSION (1) In the present invention, transgenes were constructed from the RdRp conserved region of WSMoV and broad-spectrum resistant transgenic tobacco plant lines were generated from the transgenes through Agrobacterium-mediated transformation. Some of the broad-spectrum resistant transgenic tobacco lines were highly resistant against or immune to all five tospoviruses, WSMoV, TSWV, GRSV, INSV and PCFV, tested in the examples.

(2) Application of the Present Invention in Other Plants

Other than the tobacco plants of Nicotiana benthamiana, the use of the tospoviral nucleic acid molecule in accordance with the present invention has also been applied in tomatoes, melons and watermelons, and may also be applied in peppers, cucumbers and other tospoviral host plants.

Transgenic tomato, melon, and watermelon lines carrying the transgenes described in this invention also exhibited high levels of broad-spectrum resistance, including immunity, similar to that of transgenic tobacco plants (*N. benthamiana*).

Therefore, the use of the nucleic acid molecule in accordance with the present invention provides transgenic plants with high levels of broad-spectrum resistance against phylogenetically distant or heterologous tospoviruses. The utilities of the nucleic acid molecule can be employed as feasible strategies for different crops against agricultural sufferings caused by tospoviruses.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method of obtaining a transgenic plant with a broad-spectrum resistance comprising the steps of:
   (a) obtaining an inverted repeat transgene comprising SEQ ID NO: 16;
   (b) introducing the inverted repeat transgene into a plant to generate a transgenic plant;
   (c) culturing the transgenic plant; and
   (d) selecting a transgenic plant with a broad-spectrum resistance.

* * * * *